US00PP21200P2

(12) United States Plant Patent
Shiflett

(10) Patent No.: US PP21,200 P2
(45) Date of Patent: Aug. 17, 2010

(54) CHERRY TREE, NAMED 'SR 500'

(50) Latin Name: *Prunus avium L*
Varietal Denomination: SR 500

(76) Inventor: Tom Shiflett, 6025 Loop Rd., Wenatchee, WA (US) 98801

( * ) Notice: Subject to any disclaimer, the term of this patent is extended or adjusted under 35 U.S.C. 154(b) by 0 days.

(21) Appl. No.: 12/381,339

(22) Filed: Mar. 10, 2009

(51) Int. Cl.
*A01H 5/00* (2006.01)

(52) U.S. Cl. ..... Plt./181

(58) Field of Classification Search ..... Plt./181
See application file for complete search history.

(56) References Cited

U.S. PATENT DOCUMENTS

PP11,392 P 5/2000 Lane
PP15,386 P2 11/2004 Brown

*Primary Examiner*—Annette H Para
(74) *Attorney, Agent, or Firm*—Wells St. John P.S.

(57) ABSTRACT

A new and distinct variety of cherry tree is described and which bears fruit which is ripe for harvesting and shipment under the ecological conditions prevailing in central Washington during the third week of August.

4 Drawing Sheets

BACKGROUND OF THE NEW VARIETY

The present invention relates to a new and distinct variety of cherry tree '*Prunus avium* L' and which has been denominated varietally as 'SR 500' and more specifically to a cherry tree which matures for harvesting and shipment approximately three weeks after the Bing cherry tree (unpatented) when grown under the ecological conditions prevailing in central Washington State.

DISCOVERY AND ASEXUAL REPRODUCTION

The present variety of cherry tree was discovered in 1979 as a whole tree mutation growing within the cultivated region of a block of Bing cherry trees (unpatented) which were then growing on mazzard rootstock (unpatented) at the inventor's orchard which is located at Wenatchee Heights, Chelan County, Wash. This whole tree mutation was first identified when the inventor noted that this mutated tree produced fruit which were ripe for harvesting and shipment approximately 20 days later than the adjacent Bing cherry trees (unpatented). Following the discovery, and after a number of years of observation, the inventor, in late 2002, asexually reproduced the new variety by grafting the new variety onto two year old Skeena cherry trees (U.S. Plant Pat. No. 11,392) which were then growing on mazzard rootstock (unpatented). These same Skeena cherry trees were located some three miles from the original chance mutated tree, but were located at an elevation which was some 500 feet lower than the original mutated tree. Subsequently, the inventor has studied the fruit produced from these second generation trees, which was first produced in 2005, until the current time, and has found the characteristics of these second generation trees to be identical to that of the original chance mutated tree.

SUMMARY OF THE VARIETY

The 'SR 500' cherry tree is characterized principally as to novelty by producing a novel shaped fruit which is ripe for harvesting and shipment approximately three weeks after the Bing cherry tree when grown under the ecological conditions prevailing in central Washington. Still further, the variety is distinctive by having a trunk which has an extremely rough bark texture; a reniform fruit shape; and fruit which have a darker skin and flesh color; a higher brix level; and lower acids concentration when compared to the other cherry varieties that it is most closely similar to. The new variety of cherry tree is also clearly distinguishable from other common cherry cultivars maturing at approximately the same season. In this regard, the present variety is characterized, at least in part, as to novelty by it's distinctive reniform fruit shape in comparison to the fruit produced by the Staccato cherry tree (unpatented); and the Brown cherry tree (U.S. Plant Pat. No. 15,386). Further, the present variety is distinctive relative to the Sweetheart cherry tree (Patent Pending) by producing fruit that has a darker skin and flesh color than the other varieties (FIGS. 4 and 5). Still further, the new variety produces fruit that have a higher sugar level than that of the varieties, noted above, and appreciably lower acid levels then that of the RR2A cherry tree (US Plant Patent pending) which matures in approximately the same season. Additionally, the present variety has a fruit firmness that is lower then that produced by the RR2A cherry tree (US Plant Patent Pending) or that of the Brown cherry tree (U.S. Plant Pat. No. 15,386).

BRIEF DESCRIPTION OF THE DRAWINGS

The accompanying drawings are color photographs of various aspects of the present cherry tree. The colors are as nearly true as is reasonably possible in color representations of this type. Due to chemical development, processing and printing, the leaves and fruit color of the present tree may or may not be accurate when compared with the actual specimens. For this reason, future color references should be made to the color plates provided by The Royal Horticulture Society Colour Charts (3$^{rd}$ Edition) provided by the Royal Horticulture Society of Great Britain.

DETAILED DESCRIPTION

Figure 1:
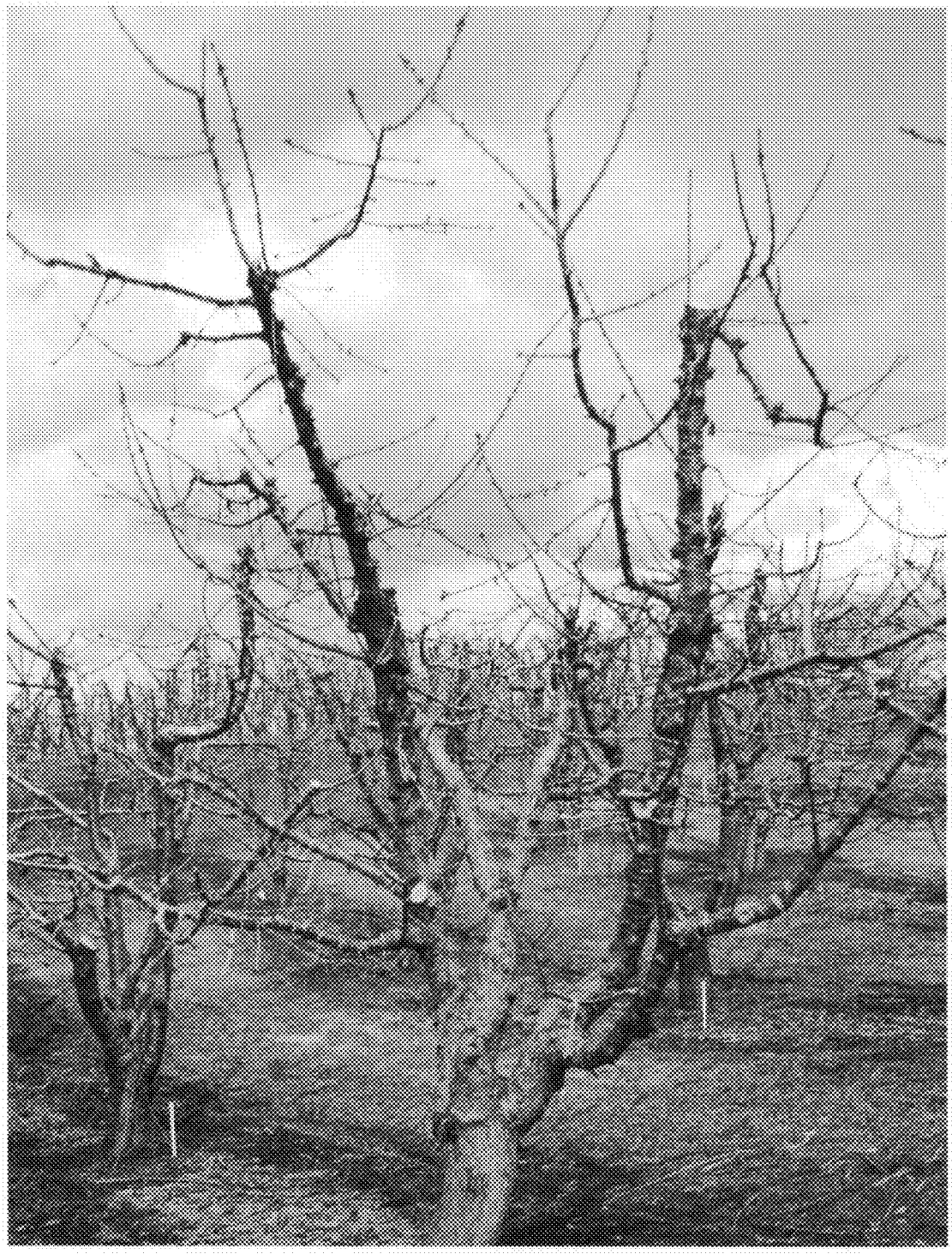
FIG. 1 depicts the original chance mutated 29 year old 'SR 500' cherry tree as seen growing in the original orchard of origin.
Figure 2:
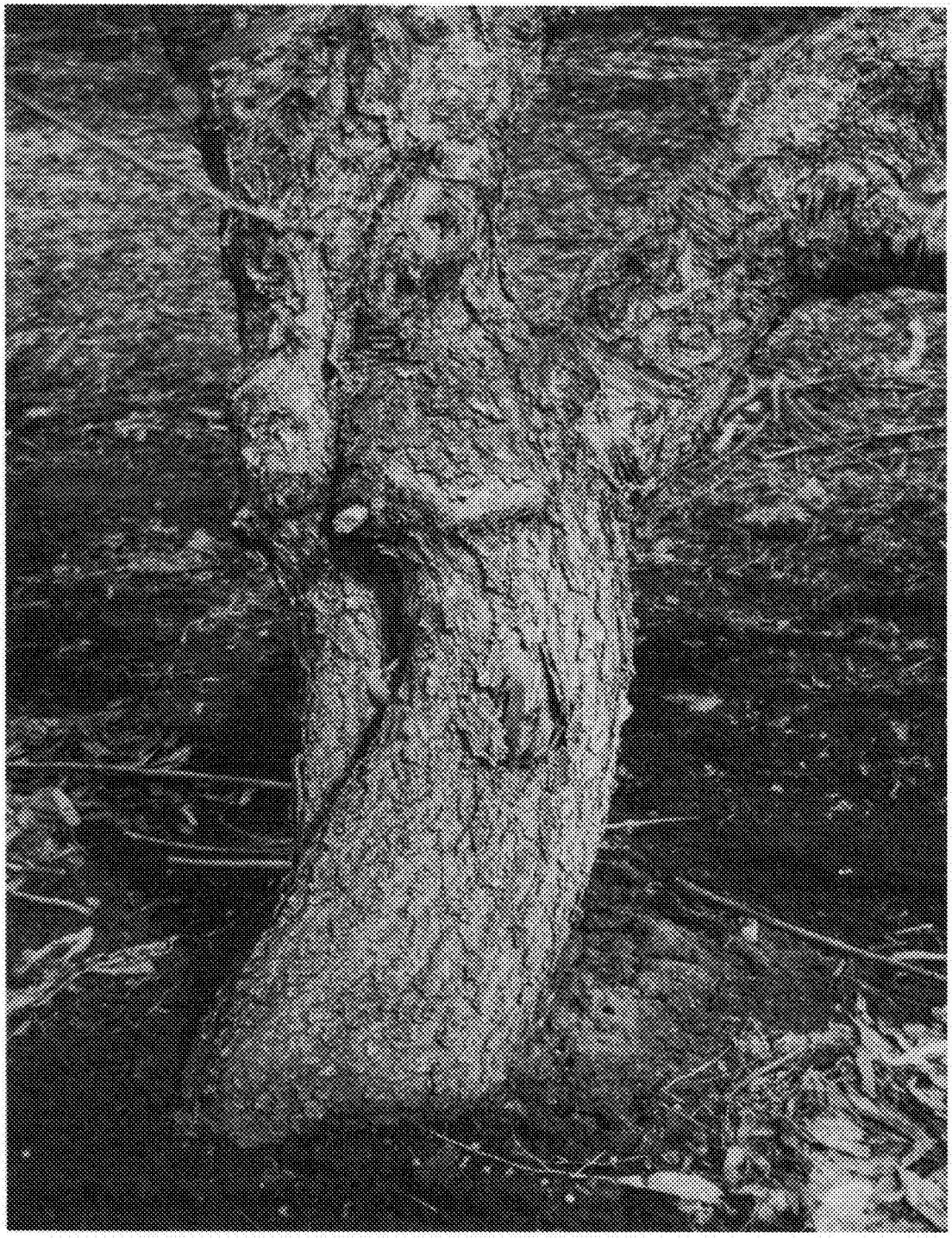
FIG. 2 shows the trunk and bark characteristics of the original chance mutated tree.
Figure 3:
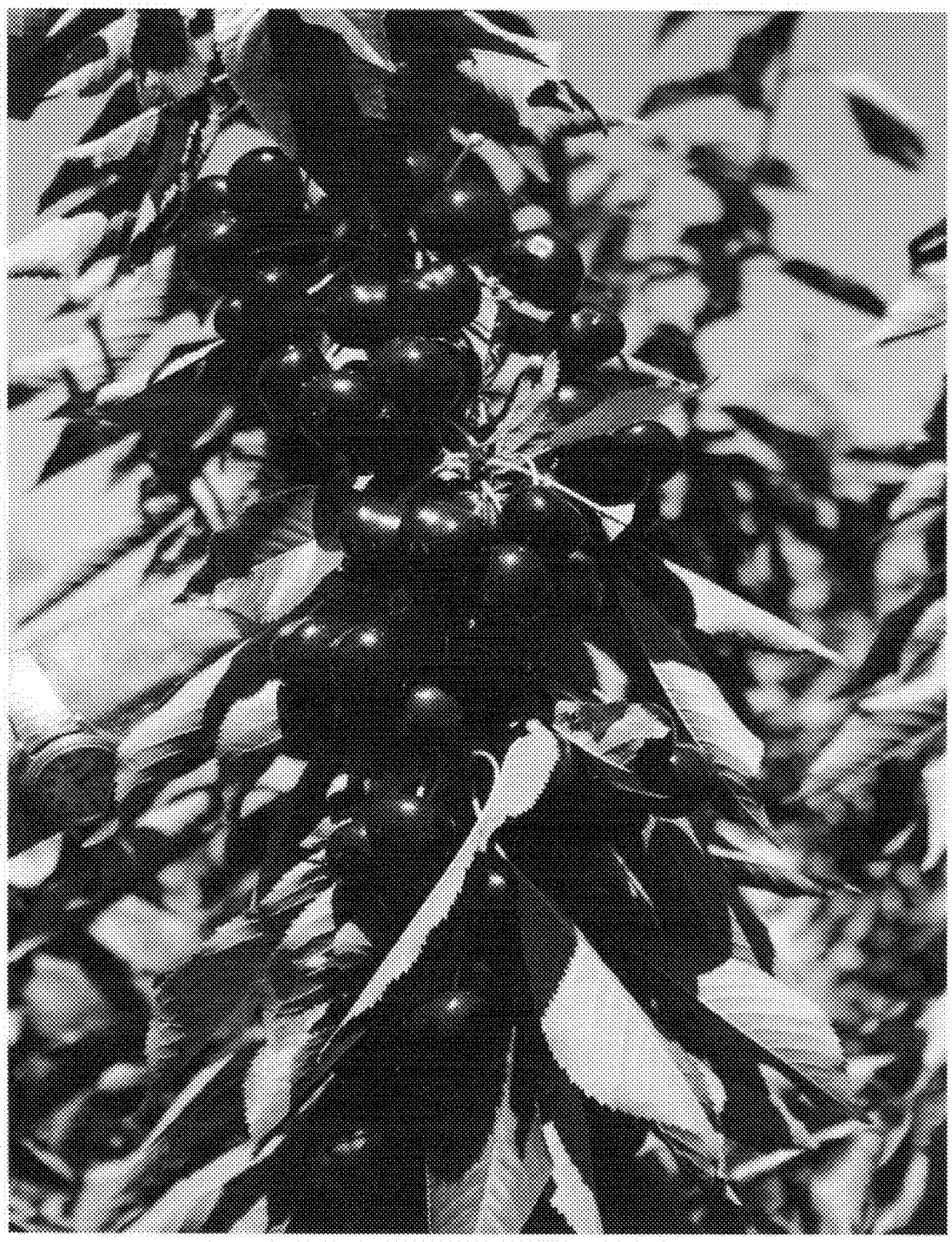
FIG. 3 depicts a fruiting branch of the new variety of cherry tree at commercial maturity.
Figure 4:
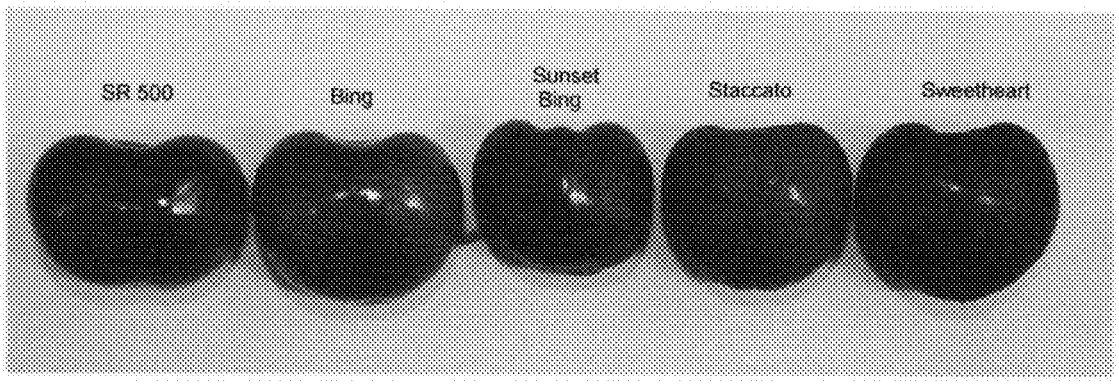
FIG. 4 shows the fruit produced by the present variety of cherry tree; the fruit produced by a Bing cherry tree (unpatented); Sunset Bing cherry tree (unpatented); Staccato cherry tree (unpatented); and the Sweetheart cherry tree (Plant Patent Pending).
Figure 5:
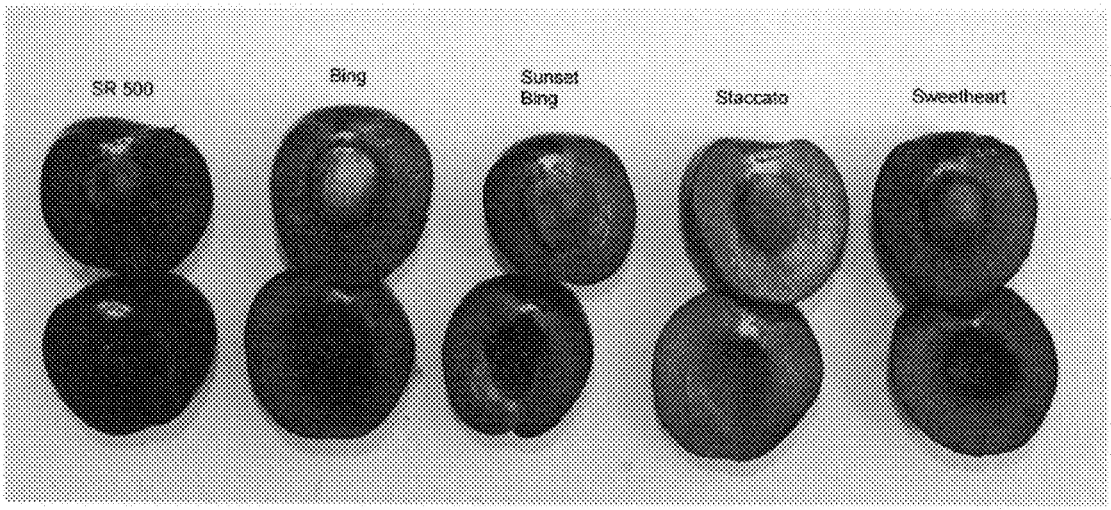
FIG. 5 shows the fruit produced by the present variety of cherry tree, and which is sectioned in the equatorial plane to display the flesh and stone characteristics thereof, and shown in comparison to the fruit produced by the Bing cherry tree (unpatented); Sunset Bing cherry tree (unpatented); Staccato cherry tree (unpatented); and the Sweetheart cherry tree (Plant Patent Pending).

Referring more specifically to the horticultural and botanical details of this new and distinct variety of cherry tree, the following characteristics have been observed under the ecological conditions prevailing at the orchard of origin which is located in Chelan County, Washington state. As indicated above, all major color code designations are by reference to the Royal Horticulture Society of Great Britain. Common color names are also used occasionally.

NOT A COMMERCIAL WARRANTY

The following detailed description has been prepared to solely comply with the provisions of 35 U.S.C. §112, and does not constitute a commercial warranty, (either expressed or implied), that the present variety will in the future display the botanical, fruiting or other characteristics as set forth, hereinafter. Therefore, this disclosure may not be relied upon to support any future legal claims including, but not limited to, beach of warranty of merchantability, or fitness for any particular purpose, or non-infringement which is directed, in whole, or in part, to the present variety.

TREE

*Size.*—Considered medium-large for the species. The present tree which is grown on mazzard rootstock (unpatented) is approximately 29 years old. The size of the tree is very similar to the adjacent Bing cherry trees (unpatented) which are growing in the same orchard of origin.

*Vigor.*—Average for the species and when grown under the current ecological conditions prevailing in central Washington state.

*Branching habit.*—Considered upright.

*Density.*—Average for the species and appears similar to the adjacent Bing cherry trees (unpatented) growing in the same orchard of origin.

*Tree form.*—Trained and pruned to an open-vase shape.

*Hardiness.*—Hardy under the ecological conditions prevailing in central Washington state. The hardiness appears similar to the adjacent Bing cherry trees (unpatented) growing in the same orchard of origin.

*Fruit production.*—Considered very precocious. The present fruit production appears to be slightly greater then that of the adjacent Bing cherry trees (unpatented) growing in the same orchard.

*Fruit bearing.*—Considered regular and consistent.

TRUNK

*Size.*—Stocky and having a diameter of about 31.6 cm. when measured at a distance of about 30.0 cm. above the surface of the earth, and at full harvest maturity.

*Bark texture.*—Considered very rough.

*Bark color.*—Brown (RHS N200C).

*Lenticels.*—Not discernable on the bark.

BRANCHES

*Surface texture.*—When measured at harvest maturity, the bark texture is smooth, which is very typical of cherry trees, in general.

*Scaffold branches.*—Bark texture — Considered smooth and having numerous large lenticels. This is quite typical of cherry trees.

*Scaffold branches.*—Size — Ranging from about 6.5 cm. to about 7.25 cm. in diameter.

*Scaffold branches.*—Bark color — Grey-orange (RHS 166A).

*Scaffold branches.*—Lenticels — Considered large and numerous.

*Scaffold branch lenticels.*—Length — About 20.6 mm.

*Scaffold branch lenticels.*—Width — About 5.5 mm.

*Scaffold branch lenticels.*—Color — Grey-orange (RHS 166C).

*Fruiting branches.*—Surface texture — Considered smooth.

*Fruiting branches.*—Color — Brown (RHS 200D).

*Fruiting branches.*—Lenticels — Moderate in number, (about 6 per square cm.).

*Fruiting branch lenticels.*—Shape — Round.

*Fruiting branch lenticels.*—Diameter — Average, about 0.75 mm. to about 1 mm.

*Fruiting branch lenticels.*—Color — White (RHS N155C).

*Current season branches.*—Size — Approximately 21.1 cm. in length, and about 4.9 mm. in diameter, when measured at approximately the middle of the branch.

*Current season branch color.*—Grey-brown (RHS N199D).

*Current season branch lenticels.*—Generally speaking, they are few in number, that is, about 2 lenticels per square cm. of surface area.

*Current season branch lenticels.*—Size — On average, these are about 0.5 mm. in diameter.

*Current season branch lenticels.*—Color — White (RHS N155C).

LEAVES

*Size.*—Considered large for the species, and averaging about 15.2 cm. in length, and about 6.7 mm. in width.

*Surface texture.*—Smooth.

*Leaf tip shape.*—Acuminate.

*Leaf base shape.*—Rounded.

*Leaf form.*—Considered oblong.

*Marginal form.*—Bi-serrate.

*Leaf blade color.*—Upper surface — Yellow-green (RHS 147A).

*Leaf blade color.*—Lower surface — Yellow-green (RHS 147B).
*Leaf mid-vein.*—Size — Considered large for the species and having an average diameter of about 1.5 mm. when measured at a distance of about 4 cm. from the base of the blade.
*Mid-vein color.*—Yellow-green (RHS 149D).
*Leaf petiole.*—Length — About 39.7 mm.
*Leaf petiole.*—Diameter — About 2 mm. when measured at the midpoint of same.
*Leaf petiole.*—Surface texture — Upper surface is grooved.
*Leaf petiole.*—Upper surface color — Grey-red (RHS 182B).
*Leaf petiole.*—Lower surface color — Yellow-green (RHS 149D).
*Leaf glands.*—Generally — Present, and kidney shaped.
*Leaf glands.*—Length — About 2.4 mm.
*Leaf glands.*—Width — About 1.7 mm.
*Leaf glands.*—Numbers — On average, 2 appear per petiole.
*Leaf glands.*—Location — About 0.5 to about 1 cm. from the leaf blade base.
*Leaf glands.*—Positions — Alternating and occasionally a few opposite ones may be found.
*Leaf glands.*—Color — Grey-red (RHS 179A).
*Leaf stipules.*—Not present.

FLOWER

*Flower buds.*—Numbers — On each fruiting spur, the number of flower buds range from about 2 to about 7.
*Flower buds.*—Hardiness — Considered much hardier than those of the Bing cherry tree (unpatented) which were growing in the same orchard.
*Flower bud.*—Length — About 8.8 mm.
*Flower bud.*—Width — About 4.5 mm.
*Flower bud form.*—Plump and conical.
*Date of first bloom.*—About May 8$^{th}$ under the ecological conditions prevailing in central Washington state.
*Date of full bloom.*—About May 13$^{th}$ under the current ecological conditions prevailing in central Washington state.
*Flower size.*—At full bloom, the flowers are about 36 mm. in diameter. The flower form is considered to be fully opened.
*Bloom count.*—Generally — Variable, from 2 to 4 blossoms may be found per bud.
*Flower petals.*—Numbers — 5.
*Flower petals.*—Color — White (RHS N155C).
*Flower petals.*—Length — On average, about 16.4 mm.
*Flower petals.*—Width — On average, about 11.1 mm.
*Nectaries.*—Color — Yellow-green (RHS 144B).
*Stamens.*—Filaments — Numerous, on average about 28.
*Filament color.*—Yellow-green (RHS 145D).
*Anther.*—Shape — Kidney shaped and having an average size of about 0.5 mm. in width, and about 0.75 mm. in length.
*Pollen.*—Amount — Considered abundant.
*Pollen.*—Color — Yellow (RHS 3D).
*Carpel.*—Style length — About 11.5 mm.
*Style.*—Color — Yellow-green (RHS 144D).
*Stigma.*—Shape — Club-like.
*Stigma.*—Diameter — About 0.92 mm.
*Stigma.*—Color — Yellow-green (RHS 152A).
*Sepals.*—Numbers — 5.
*Sepals.*—Form — Cupped inwardly, and folded back toward the thalamus when the petals are fully opened.
*Sepals.*—Width — About 4 mm.
*Sepals.*—Length — About 7.8 mm.
*Sepals.*—Color — Yellow-green (RHS 143C). However, the outside tips have a red-purple color (RHS 59A).
*Peduncle.*—Length — About 17.3 mm.
*Peduncle.*—Color — Yellow-green (RHS 144B).

FRUIT

*Maturity when described.*—Ripe for harvesting and shipment approximately August 25, under the ecological conditions prevailing in central Washington. This date of maturity is approximately three weeks after the Bing cherry trees (unpatented) which are growing in the orchard of origin. Further, this is about 2 weeks later than the Sweetheart cherry tree (US Plant Patent applied for) and the Sunset Bing cherry tree (U.S. Plant Pat. No. 15,386) growing at the same location. This date of harvesting is similar to that of the Staccato cherry tree (unpatented) and the RR2A cherry tree (Patent Pending) which are growing at this location.
*Fruit size.*—Generally — Considered medium-large for the species, about a peak size or 9.05.
*Suture diameter.*—About 29.4 mm.
*Average apex diameter.*—About 23.1 mm.
*Fruit form.*—Considered uniform.
*Fruit shape.*—Reniform.
*Suture.*—Generally — The fruit suture is very shallow and has no raised portion and is nearly visually indistinct.
*Fruit base.*—Shape — Rounded and deeply indented.
*Peduncle cavity depth.*—About 3.7 mm.
*Fruit apex.*—Shape — Rounded, and ending in a flat apex.
*Peduncle.*—Length — Considered medium short in length and thin, about 2.5 cm. long.
*Peduncle.*—Color — Green (RHS 138C).
*Fruit skin.*—Thickness — Considered average for the species.
*Fruit skin.*—Texture — Medium and non-distinctive.
*Skin.*—Tenacious to Flesh — Yes.
*Skin.*—Tendency to Crack — Similar to the fruit produced by the Bing cherry tree (unpatented).
*Skin down.*—Wanting.
*Skin color.*—Near purple (RHS N77A).
*Flesh color.*—Grey-purple (RHS 187A).
*Pit cavity color.*—Grey-purple (RHS N186A).
*Flesh texture.*—Firm and crisp.
*Average firmness.*—About 329 milligrams. This is determined by Firm Tech 2 Tester. This rating is based on the pressure (in milligrams) needed to depress the flesh 1 mm.
*Flesh fibers.*—Generally speaking, they are moderate in number.
*Flesh ripening.*—Considered even.
*Flesh flavor.*—Sweet and sub-acid.
*Flesh pH.*—About 4.21.
*Flesh aroma.*—Slight.
*Flesh eating quality.*—Considered very good.

*Brix.*—About 23.4 in comparison to a brix of 21.1 for the fruit produced by the Bing cherry trees growing in the same orchard of origin.

STONE

*Type.*—Clingstone.

*Stone size.*—Considered medium for the species. About 10.2 mm. when measured between the base to the helium. About 8.3 mm. wide when measured from shoulder-to-shoulder, and about 9.8 mm. wide when measured suture-to-suture.

*Stone form.*—Considered narrowly elliptical.

*Stone base shape.*—Rounded.

*Stone helium.*—Oblong in shape.

*Stone apex.*—Shape — Rounded.

*Stone sides.*—Shape — Considered equal.

*Stone surface texture.*—Considered smooth.

*Stone.*—Ventral Edge — Generally speaking, a suture appears and is mostly sunken and subtended by two low ridges which converge basally, and apically, and which further have an average width of about 4.8 mm. when measured at mid-point. These ridges are again subtended by two partial ridges which extend from the base to approximately half the distance to the apex. These are approximately 4.8 mm. wide at the widest point.

*Stone.*—Dorsal edge — A distinct smooth and slightly raised ridge extends from the base to the apex. It is about 0.4 mm. high, and about 0.4 mm. wide.

*Stone color.*—Grey-orange (RHS 164B).

*Tendency to split.*—Not observed.

*Fruit use.*—Useful for the late season premium fresh market.

*Fruit keeping quality.*—Considered very good, and up to 30 days under common refrigeration storage conditions.

*Resistance to insects and diseases.*—The present variety shows no unusual susceptibility nor resistance to any of the common diseases or pests for such trees which are prevalent to central Washington State.

*Shipping quality.*—Considered excellent.

Although the new cherry tree possesses the described characteristics when grown under the conditions prevailing in Chelan County in central Washington State, it should be understood that variations of the usual magnitude and characteristics which are incident to changes in growing conditions, fertilization, pruning and pest control are to be expected.

Having thus described and illustrated my new variety of cherry tree, what I claim is new, and desire to secure by Plant Letters Patent is:

1. A new and distinct variety of cherry tree substantially as illustrated and described, and which bears fruit which are ripe for harvesting and shipment under the ecological conditions prevailing in Chelan County, in central Washington about the third week of August.

* * * * *